United States Patent
Schultz

(10) Patent No.: US 9,254,096 B2
(45) Date of Patent: Feb. 9, 2016

(54) METHOD AND DEVICE FOR EVALUATING AN INTENSIVE EEG OR AN EEG DURING ANAESTHESIA

(76) Inventor: Arthur Schultz, Adelheidsdorf (DE)

(*) Notice: Subject to any disclaimer, the term of this patent is extended or adjusted under 35 U.S.C. 154(b) by 458 days.

(21) Appl. No.: 13/121,249

(22) PCT Filed: Sep. 29, 2009

(86) PCT No.: PCT/DE2009/001367
§ 371 (c)(1),
(2), (4) Date: Mar. 28, 2011

(87) PCT Pub. No.: WO2010/034305
PCT Pub. Date: Apr. 1, 2010

(65) Prior Publication Data
US 2011/0178421 A1    Jul. 21, 2011

(30) Foreign Application Priority Data
Sep. 29, 2008 (DE) .................. PCT/DE2008/001594

(51) Int. Cl.
| | |
|---|---|
| *A61B 5/04* | (2006.01) |
| *A61B 5/0476* | (2006.01) |
| *A61B 5/00* | (2006.01) |
| *A61B 5/0478* | (2006.01) |

(52) U.S. Cl.
CPC ............. *A61B 5/0476* (2013.01); *A61B 5/4094* (2013.01); *A61B 5/4821* (2013.01); *A61B 5/6843* (2013.01); *A61B 5/7264* (2013.01); *A61B 5/0478* (2013.01); *A61B 5/721* (2013.01)

(58) Field of Classification Search
USPC ........................................................ 600/544
See application file for complete search history.

(56) References Cited

U.S. PATENT DOCUMENTS

| | | | | |
|---|---|---|---|---|
| 4,502,492 | A | * | 3/1985 | Bornzin .................. 607/121 |
| 4,678,865 | A | | 7/1987 | Sherwin |
| 4,846,190 | A | | 7/1989 | John |
| 5,978,693 | A | * | 11/1999 | Hamilton et al. ............ 600/391 |

(Continued)

FOREIGN PATENT DOCUMENTS

| | | |
|---|---|---|
| EP | 0 856 181 B1 | 3/1999 |
| EP | 1 795 122 A1 | 6/2007 |

OTHER PUBLICATIONS

Gramatica et al. ("Micropatterned non-invasive dry electrodes for Brain-Computer Interface", Proceedings of the 3rd IEEE-EMBS International Summer School and Symposium on Medical Devices and Biosensors, Sep. 2006).*

*Primary Examiner* — Etsub Berhanu
(74) *Attorney, Agent, or Firm* — Whitham Curtis Christofferson & Cook, PC

(57) ABSTRACT

A computer implemented method and system is used for evaluating an intensive EEG or an EEG during anaesthesia. Time domain and/or frequency range parameters are determined from the EEG graphs. The determined parameters are used in multivariate classification functions and the intensive EEG or EEG during anaesthesia are automatically divided into stages. The EEG graphs are also analysed for interfering signal components from the quantity of biosignals of graphs characteristic of intensive EEGs or EEGs which are not performed during anaesthesia. If interfering signal components are identified, the existence of biosignals of graphs characteristic of intensive EEGs or EEGs which are not performed during anaesthesia is verified by artifact analysis in the absence of artifacts, and is not verified if artifacts are identified.

22 Claims, 2 Drawing Sheets

(56) References Cited

U.S. PATENT DOCUMENTS

| | | | |
|---|---|---|---|
| 6,011,990 A * | 1/2000 | Schultz et al. | 600/544 |
| 6,473,639 B1 | 10/2002 | Fischell et al. | |
| 6,731,975 B1 * | 5/2004 | Viertio-Oja et al. | 600/544 |
| 2001/0048139 A1 * | 12/2001 | Aigner et al. | 257/415 |
| 2003/0171661 A1 * | 9/2003 | Tong | 600/300 |
| 2007/0197930 A1 * | 8/2007 | Sarkela | 600/544 |
| 2008/0077191 A1 * | 3/2008 | Morrell | 607/45 |

* cited by examiner

METHOD AND DEVICE FOR EVALUATING AN INTENSIVE EEG OR AN EEG DURING ANAESTHESIA

The invention relates to a method for evaluating an anesthesia EEG or intensive-care EEG, in which parameters from the time and/or frequency domain are established from the EEG curves by inserting the established parameters into multivariate classification functions and as a result stages of the anesthesia EEG or intensive-care EEG being classified automatically, and to device for evaluating an anesthesia EEG or intensive-care EEG by means of a computer, which establishes parameters from the time and/or frequency domain from the measured EEG curves, inserts the established parameters into multivariate classification functions and automatically classifies stages of the anesthesia EEG or intensive-care EEG from this.

BACKGROUND

EP 0 856 181 B1 has disclosed a method and a device for evaluating an anesthesia EEG or intensive-care EEG. The anesthesia EEG or intensive-care EEG is classified from EEG curves by means of mathematical-statistical methods. Moreover, artifacts are registered and taken into account for correcting or suppressing classifications.

EP 1 795 122 A1 has disclosed the practice of registering EEG signals and bio-impedance signals. Instances where a bio-impedance threshold is exceeded or the similarity between the signals in the EEG signal and in the bio-impedance signal is/are used for artifact recognition. The bio-impedance analysis can be used to discard EEG signal sections that are subjected to artifacts, or the classification as "awake" can be supported, for example if blinking eyes are identified. This document predominantly relates to artifacts in the facial region.

U.S. Pat. No. 6,731,975 A has disclosed a method for determining the cerebral status of a patient, for example after an anesthetic is administered. To this end, the entropy in the EEG signal and in the combined EEG-EMG signal, and a pure EMG index, are calculated.

It was found that there are a number of triggers for bio-signals, which can modify EEG curves and interfere with a classification of the anesthesia EEG or intensive-care EEG. Volatile anesthetics on the basis of flurane, in particular sevoflurane, should be highlighted since these can trigger seizure potentials with increasing dosage.

SUMMARY

The invention is based on the object of being able to identify bio-signals when evaluating an anesthesia EEG or intensive-care EEG and being able to differentiate these bio-signals from artifacts.

In the case of a method for evaluating an anesthesia EEG or intensive-care EEG according to the preamble of claim 1 and a device for evaluating an anesthesia EEG or intensive-care EEG according to the preamble of claim 5, this object is achieved by the characterizing features of the respective claim.

Developments and advantageous embodiments emerge from the respective dependent claims.

In the solution according to the invention, parameters from the time and/or frequency domain are still established from the EEG curve profiles and inserted into multivariate classification functions. In the process, there is an automatic classification into stages of an anesthesia EEG or intensive-care EEG. However, the curve profiles are moreover also examined in respect of scattering-in signal components. Scattering-in signal components are those that influence the overall curve profile but are atypical for an anesthesia EEG or intensive-care EEG and the origin thereof is also different to that for the anesthesia EEG or intensive-care EEG typical or characteristic curves.

The scattered-in signals may be bio-signals of a different origin or resulting from artifacts, which respectively modify the curve profiles of the actual anesthesia EEG or intensive-care EEG. In order to find out whether the scattered-in signals could be bio-signals and/or artifacts, an artifact analysis is additionally carried out if scattering-in signals are detected. Methods and procedures known per se may be used for artifact analysis. Should the evaluation demonstrate that there are no artifacts present, it follows from a reverse argument that the scattered-in signals stem from bio-signals that are not from anesthesia EEG or intensive-care EEG characteristic curves. By contrast, if artifacts are detected, these scattered-in signals can only be caused by artifacts or by the combination of artifacts and bio-signals. Unambiguous verification of the existence of bio-signals is not possible in this case, and hence both cases are treated equally by not verifying the existence of bio-signals if artifacts are detected.

When bio-signals are verified, the analysis of these bio-signals of non-anesthesia EEG or non-intensive-care EEG characteristic curves can be carried out by comparing the EEG curves generated by the scattering-in bio-signals with corresponding features of stored graphical patterns of curve profiles of various bio-origins.

It was found that not all bio-signals can be characterized to the same extent by establishing parameters from the time and/or frequency domain and inserting these into multivariate functions.

This particularly holds true for bio-signals whose profile deviates from the curve profile of an anesthesia EEG or intensive-care EEG. In this case another type of analysis is more meaningful, specifically a graphical comparison of the curve profile of scattering-in bio-signals with stored patterns of signal profiles of different bio-signals. By comparing features of stored graphical patterns, the scattering-in bio-signals can then be associated with a stored pattern, wherein the link of the known origin of the stored pattern also allows a deduction of the origin of the analyzed bio-signal.

If bio-signals exist, these signal components can preferably be analyzed in respect of curve profiles that are typical for epilepsy. As a result, this affords the possibility of identifying possible epilepsy-typical scattered-in signals, which can be caused by administered drugs, in an anesthesia EEG or intensive-care EEG, which has scattered-in signals from further bio-signals.

As per one development, shape modifications of lead electrodes can be recorded and evaluated as artifacts.

Such changes in shape may influence the voltages discharged from the lead electrodes as a result of charge transfers and changes in the conductivity between lead electrode and skin. By registering changes in shape, simultaneous influences of the discharged voltages can be identified as artifacts.

Bio-signals that have non-anesthesia EEG or non-intensive-care EEG characteristic curves, for example curve shapes that are typical for epilepsy, can be distinguished by steep amplitude-time transitions; these can also occur as a result of artifacts at the lead electrodes, for example if the electrodes or the lines thereof are moved by mechanical means.

By registering shape modifications of lead electrodes, the most common artifacts in practice can be identified and evaluated as evidence for whether scattering-in signals are artifacts or bio-signals.

The verification becomes more reliable by a direct qualitative or else quantitative comparison.

The deformation sensors for registering shape modification signals may comprise capacitances, which can be changed by deformation and the change in capacitance of which correlates with the deformation of the EEG electrodes.

Using capacitances as deformation sensors allows registering and amplifying shape modification signals using the conventional EEG signal amplifier and subsequent computer-assisted evaluation.

The capacitances preferably consist of adjacent connection lines and insulations, respectively constituting a dielectric and arranged between the connection lines.

This allows conductor-dielectric components of a multi-electrode arrangement to be used additionally as deformation sensors.

Additionally, the EEG electrodes may comprise skin preparation means, which reduce deformation-dependent conductivity changes between the electrode surface and the skin.

The skin preparation means reduce an influence of changes in the conductivity between lead electrode and skin on the voltages discharged by the lead electrodes.

The skin preparation means are preferably surface-increasing invaginations and/or evaginations of the electrode surface.

The skin preparation means make the skin surface at the contact site of the electrode accessible for a deeper penetration of conductive electrode gel by stripping away and breaking up. As a result, the effective contact area is increased, as a result of which deformation-dependent conductivity changes of parts of the contact surface have less influence on the overall conductivity.

In the following text, the invention will be explained on the basis of a flowchart and an exemplary embodiment, which is illustrated in the drawing.

DETAILED DESCRIPTION

Figure 1:
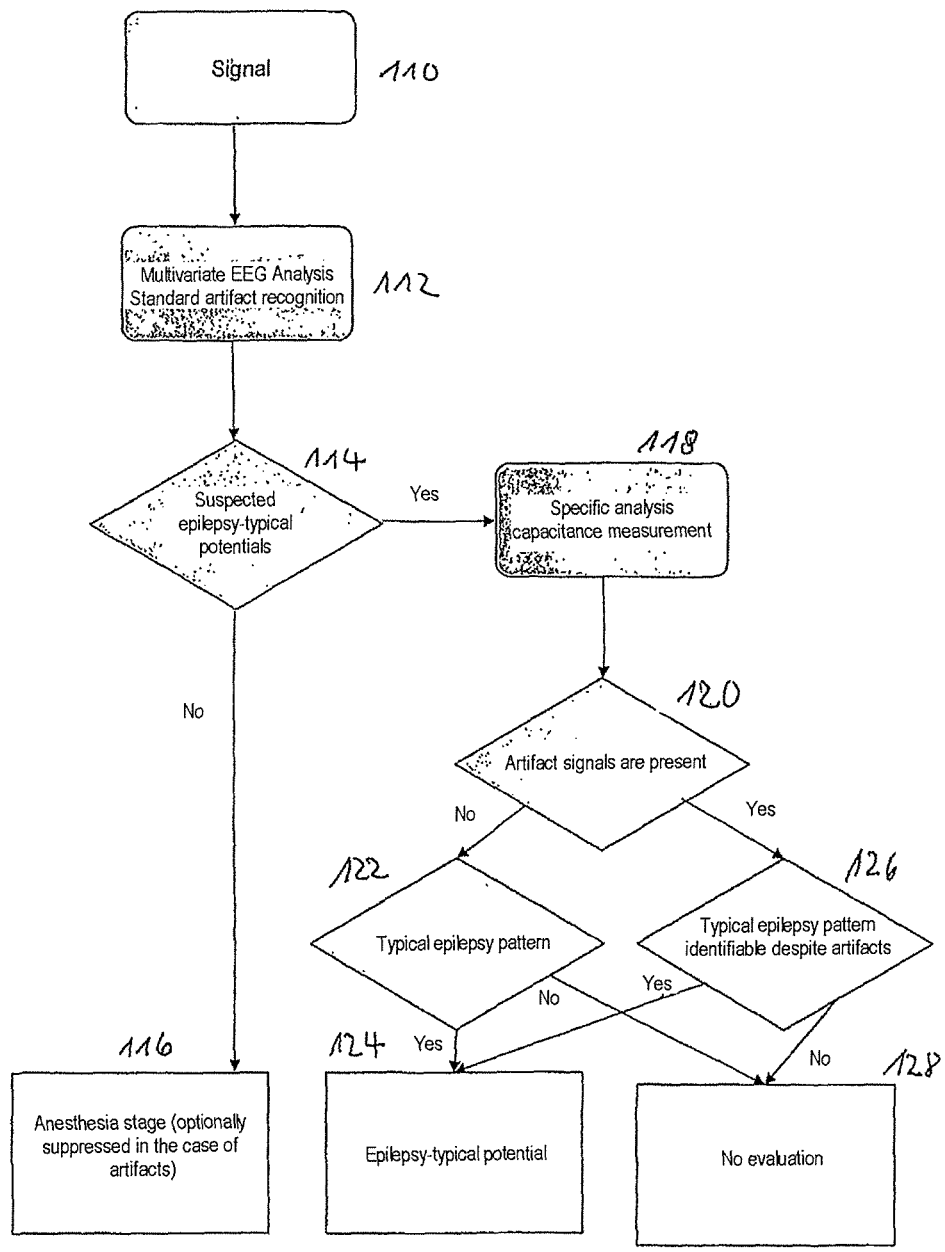
FIG. 1 shows a flowchart of the invention.

As per the flowchart illustrated in FIG. 1, an incoming signal 110 is analyzed in analysis steps 112 by parameters in the time and/or frequency domain being inserted into multivariate classification functions and stages of an anesthesia EEG or intensive-care EEG subsequently being classified automatically. Additionally, standard artifact recognition is also carried out here; taking account of this can suppress or correct a stage classification.

In a subsequent step 114, the signal is analyzed in respect of possible scattered-in signals, wherein the scattered-in signals are signal components that are not characteristic for an anesthesia EEG or intensive-care EEG and would therefore adversely affect or falsify classification. The present example relates to possible epilepsy-typical potentials.

If no scattered-in signals are detected, the stage of the anesthesia EEG and intensive-care EEG is illustrated, or optionally suppressed in the case of artifacts, at 116.

By contrast, if scattered-in signals are detected at 114, the scattered-in signals are analyzed for possible artifacts in step 118. In the present case, this is brought about by analysis by means of measuring the capacitance.

If no artifact signals are identified in the block 120, the conclusion is drawn that the scattered-in signals are bio-signals; otherwise the conclusion is drawn that these are artifacts or a combination of artifacts and bio-signals.

In the case where no artifact signals are present, the scattering-in signal is compared by comparison to a stored pattern, in this case an epilepsy pattern, in a further decision block 122. If a comparison between the signal and a stored pattern is positive, this is indicated in a block 124 as an epilepsy-typical potential; if this is not the case, it is indicated to a block 128 that no evaluation is undertaken.

If artifact signals are present, a check can optionally also still be made in a decision block 126 as to whether the bio-signal is still identified in the case of a possible combination with a bio-signal, and whether it has correspondences with a typical epilepsy pattern. In the positive case, a branch can then likewise be made to the block 124, and an epilepsy-typical potential can be indicated, or, should this not be the case or if it is not possible to identify bio-signals, a branch is made to the block 128 and no evaluation is displayed.

Figure 2:
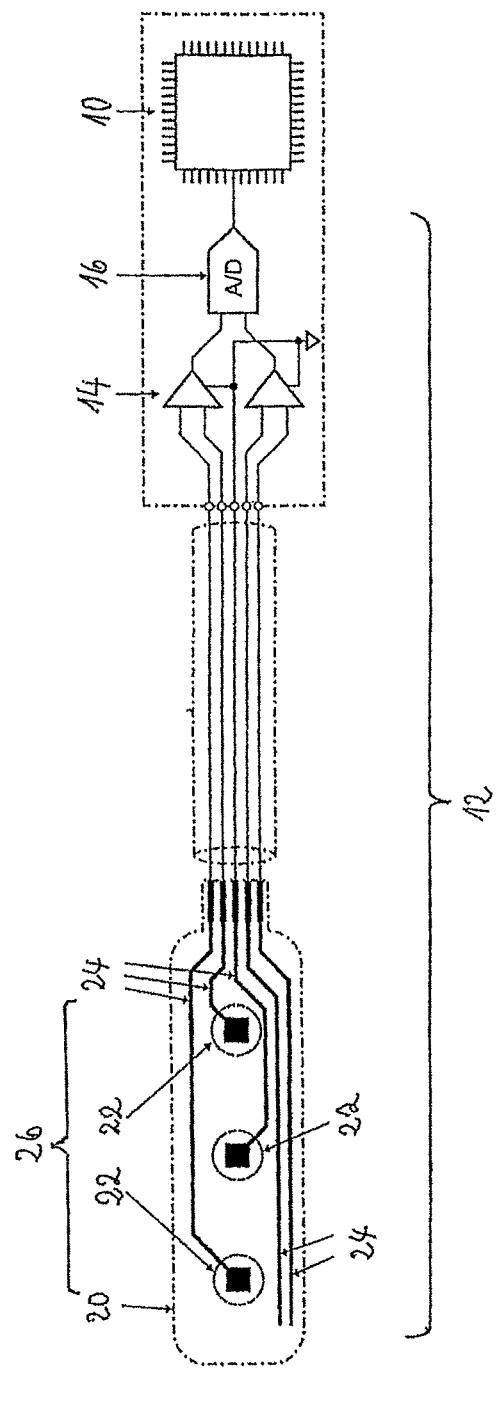
FIG. 2 shows a device made of a computer and a measuring unit for an EEG channel.

FIG. 2 shows a device comprising a computer and a measuring unit for an EEG channel.

The device consists of a computer 10 and a measuring unit 12 for an EEG channel, the measuring unit consisting of a preamplifier 14 with an analog/digital converter 16 and a multi-electrode arrangement 26 on an electrode strip 20 with three electrodes 22 and conductors 24 embedded in the electrode strip 20. By supplementing the electrode strip 20 with additional electrodes 22, it is possible to supplement discharges for further EEG channels.

The electrode strip 20 is attached to the head of a patient and connected to a preamplifier 14 with an analog/digital converter 16. The preamplifier 14 forms the differences between the potentials of the electrodes 22 and amplifies the differential potentials for matching the value range to the analog/digital converter 16.

The preamplifier 14, the analog/digital converter 16 and the computer 10 can be arranged on the electrode strip 20 and can be connected to the conductors 24 and can transmit a display signal to a monitor by telemetric means. Alternatively, the computer 10 can also be an external computer, which is coupled to the preamplifier 14 and the analog/digital converter 16 by telemetric means or by wires. If the electrode strip 20 is a disposable material, it can be replaced whilst the preamplifier 14, the analog/digital converter 16 and the computer 10 continue to be used.

Parameters from the time and/or frequency domain are established in a known fashion from the EEG curves by means of the computer 10 by inserting the established parameters into multivariate classification functions and as a result stages of the anesthesia EEG or intensive-care EEG being classified automatically.

The EEG curves are additionally analyzed in respect of curve patterns from further bio-signals, more particularly curve patterns that are typical for epilepsy.

Artifacts as shape modifications of the lead electrodes 22 are registered by measuring the capacitance between adjacent connection lines 24 of the multi-electrode arrangement 26. The capacitance can be measured by evaluating a change in voltage, amplified by the preamplifier 14, at the conductors 24 of the electrode strip 20, which conductors serve for measuring the capacitance, but not for EEG derivation. The change in voltage is the result of a charge transfer. Alternatively, it is also possible to feed an AC voltage signal, supplied by a signal generator, into a conductor pair of the connection lines 24 of the multi-electrode arrangement 26 and to measure the voltage of the AC voltage signal coupled over into another conductor pair of the connection lines 24 of the multi-electrode arrangement 26. The respectively measured change in capacitance constitutes a measure for the deformation of the lead electrodes 22.

Comparing the changes in the capacitance with the analyzed curve pattern in the EEG that is typical for epilepsy affords the possibility of determining whether the curve pattern could have been created by coupling in artifacts or whether it is more probable that it stems from brainwave activity.

The Invention claimed is:

1. A device for evaluating an electroencephalogram (EEG) from a patient under anesthesia or in intensive care, comprising:
    a measuring unit having EEG electrodes in a multi-electrode arrangement and which measures an EEG of a patient;
    artifact sensors configured for detection of shape modification signals correlating with deformation in said EEG electrodes; and
    a computer configured to perform the steps of
        establishing parameters from time and/or frequency domains from EEG curve profiles of said EEG measured with said measuring unit,
        inserting said parameters of said establishing step into multivariate classification functions to automatically classify stages of the EEG,
        performing a first analysis of said EEG curve profiles which searches for scattering-in signal components, wherein said scattering-in signal components are atypical EEG signal components, wherein atypical bio-signals and artifacts are types of atypical EEG signal components;
        performing a second analysis on search results of said first analysis which verifies if such search results are one of
            a) atypical bio-signals, or
            b) artifacts,
        wherein if scattering-in signal components are detected by the computer in said first analysis and shape modification signals are not detected by said artifact sensors, the existence of atypical bio-signals in said search results is verified in said second analysis,
        wherein said existence of atypical bio-signals in said search results is not verified if shape modification signals are detected by said artifact sensors,
        wherein said computer is further configured to provide an output based on the verification or non-verification outcome useable for display, and
        wherein said atypical bio-signals are different from said artifacts.

2. The device as claimed in claim 1, further comprising storage means with stored graphical patterns of curve profiles of various bio-origins, wherein said computer undertakes a program-controlled comparison between the EEG curve profiles containing EEG curves as two-dimensional graphics and the stored graphical patterns of the curve profiles of various bio-origins.

3. The device as claimed in claim 2, wherein if the existence of atypical bio-signals in said search results is verified, the computer further analyzes such atypical bio-signals with respect to curve profiles that are typical for epilepsy.

4. The device as claimed in claim 1, wherein the artifact sensors allow measurement of deformation of the EEG electrodes.

5. The device as claimed in claim 4, wherein the artifact sensors are deformation sensors which have a measurable capacitance, wherein a change in capacitance correlates with the deformation of the EEG electrodes.

6. The device as claimed in claim 5, wherein the deformation sensors consist of adjacent connection lines and insulations, respectively constituting a dielectric and arranged between the connection lines, of the multi-electrode arrangement.

7. The device as claimed in claim 1, wherein the EEG electrodes comprise skin preparation means made of surface-increasing invaginations of the electrode surface.

8. A computer-implemented method of analyzing an electroencephalogram (EEG) from a patient under anesthesia or in intensive care, comprising the steps of:
    recording said EEG with a measuring unit having EEG electrodes connected to said patient;
    establishing parameters from one or more of a time domain and a frequency domain from EEG curve profiles of said EEG, said EEG curve profiles containing characteristic EEG curves;
    performing, using a computer, multivariate classification using said parameters established in said establishing step to classify stages of said EEG;
    performing, using a computer, a first analysis of said EEG curve profiles which searches for scattering-in signal components, wherein said scattering-in signal components are atypical EEG signal components, wherein atypical bio-signals and artifacts are types of atypical EEG signal components;
    performing, using a computer, a second analysis on search results of said first analysis which verifies if such search results are one of
        a) atypical bio-signals, or
        b) artifacts,
        wherein said second analysis includes evaluation of shape modification signals which correlate with deformation in EEG electrodes;
    wherein if in said step of performing a second analysis no shape modification signals are identified, the computer verifies that atypical bio-signals which are not characteristic EEG curves exist in the search results;
    wherein if in said step of performing a second analysis one or more shape modification signals are identified, the computer does not verify that atypical bio-signals which are not characteristic EEG curves exist in the search results; and
    providing an output based on the verification or non-verification outcome useable for display,
    wherein said atypical bio-signals are different from said artifacts.

9. The method of claim 8, wherein said step of performing a second analysis includes measuring a capacitance of deformations sensors detecting shape modification signals correlating with deformation in said EEG electrodes to identify whether any epilepsy typical potentials are within the search results.

10. The method of claim 9, further comprising the step of checking whether a typical epilepsy pattern is identifiable despite artifacts, and
    if a typical epilepsy pattern is identified an epilepsy typical potential is indicated, and
    if no typical epilepsy pattern is identified no epilepsy typical potential is indicated.

11. The method of claim 9, wherein if a capacitance measurement determined by said step of measuring capacitance shows no artifact signals are present, there is a further step of checking whether a typical epilepsy pattern is present and
   if a typical epilepsy pattern is identified an epilepsy typical potential is indicated, and
   if no typical epilepsy pattern is identified no epilepsy typical potential is indicated.

12. The method of claim 8, further comprising the step of presenting one or more stages of said EEG curve profile which are established in said performing multivariate classification step when it is verified that atypical bio-signals which are not characteristic EEG curves exist in the search results.

13. The method of claim 8, further comprising the step of comparing the search results to one or more stored patterns typical of epilepsy.

14. The method of claim 8, further comprising the step of suppressing one or more stages of said EEG curve profile which are established in said performing multivariate classification step when shape modification signals are identified.

15. A device for analyzing an electroencephalogram (EEG) from a patient under anesthesia or in intensive care, comprising:
   a measuring unit for an EEG channel, the measuring unit comprising a preamplifier with an analog/digital converter and a multi-electrode arrangement on an electrode strip adapted for attachment to a patient, the multi-electrode arrangement being connected to the preamplifier via conductors, signals from the multi-electrode arrangement being received by the preamplifier to form differences between potentials of electrodes of the multi-electrode array and amplify differential potentials for matching a value range to the analog/digital converter which converts the differential potentials to digital inputs;
   a computer configured to receive the digital inputs and
      a) establish parameters from one or more of a time domain and a frequency domain from EEG curve profiles of an EEG, said EEG curve profiles containing characteristic EEG curves from said patient under anesthesia or in intensive care,
      b) perform multivariate classification using said parameters to classify stages of said EEG,
      c) perform a first analysis of said EEG curve profiles which searches for scattering-in signal components, wherein said scattering-in signal components are atypical EEG signal components, wherein atypical bio-signals and artifacts are types of atypical EEG signal components,
      d) perform a second analysis on search results of said first analysis to verify if such search results are one of
         i) atypical bio-signals, or
         ii) artifacts,
         wherein said second analysis includes evaluation of shape modification signals which correlate with deformation in electrodes of the multi-electrode array, and
      e) if in said step of performing a second analysis no shape deformation signals are identified, the computer provides an output which verifies atypical bio-signals which are not characteristic EEG curves exist in the search results; but
         if in said step of performing a second analysis one or more shape deformation signals are identified, the computer provides an output which does not verify atypical bio-signals which are not characteristic EEG curves exist in the search results,
         wherein said atypical bio-signals are different from said artifacts.

16. The device of claim 15, further comprising deformation sensors, wherein the second analysis by the computer includes measuring a capacitance of the deformation sensors to identify whether any epilepsy typical potentials are within the search results.

17. The device of claim 16, wherein if a capacitance measurement determined by measuring capacitance shows no artifact signals are present, the computer is further programmed to check whether a typical epilepsy pattern is present and
   if a typical epilepsy pattern is identified an epilepsy typical potential is indicated, and
   if no typical epilepsy pattern is identified no epilepsy typical potential is indicated.

18. The device of claim 15, wherein the computer is further programmed to check whether a typical epilepsy pattern is identifiable despite artifacts, and
   if a typical epilepsy pattern is identified an epilepsy typical potential is indicated, and
   if no typical epilepsy pattern is identified no epilepsy typical potential is indicated.

19. The device of claim 15, wherein the computer is further programmed so that when the computer provides an output which verifies atypical bio-signals which are not characteristic EEG curves exist in the search results, the computer further provides output of one or more stages of said EEG curve profile which are established in said step of performing multivariate classification.

20. The device of claim 15, wherein the computer is further programmed to compare said search results to one or more stored patterns typical of epilepsy.

21. The device of claim 15, wherein the computer is further programmed to suppress one or more stages of said EEG curve profile which are established in said multivariate classification when shape modification signals are identified.

22. A computer-implemented method of analyzing an electroencephalogram (EEG) from a patient under anesthesia or in intensive care, comprising the steps of:
   recording said EEG with a measuring unit having EEG electrodes connected to said patient;
   establishing parameters from one or more of a time domain and a frequency domain from EEG curve profiles of said EEG, said EEG curve profiles containing characteristic anesthesia EEG curves;
   performing, using a computer, multivariate classification using said parameters established in said establishing step to classify stages of said EEG;
   performing, using a computer, a first analysis of said EEG curve profiles which searches for scattering-in signal components, wherein said scattering-in signal components are atypical EEG signal components, wherein atypical bio-signals and artifacts are types of atypical EEG signal components;
   performing, using a computer, a second analysis on search results of said first analysis which verifies if such search results are one of
      a) atypical bio-signals which are not characteristic anesthesia EEG curves, or
      b) artifacts,
      wherein said second analysis includes evaluation of shape modification signals which correlate with deformation in EEG electrodes;
   wherein if in said step of performing a second analysis no shape modification signals are identified, the computer verifies that atypical bio-signals which are not characteristic anesthesia EEG curves exist in the search results;
wherein if in said step of performing a second analysis one or more shape modification signals are identified, the computer does not verify that atypical bio-signals which are not characteristic anesthesia EEG curves exist in the search results; and
providing an output based on the verification or non-verification outcome useable for display,
wherein said atypical bio-signals are different from said artifacts.

* * * * *